United States Patent
Schulman et al.

(10) Patent No.: US 8,024,022 B2
(45) Date of Patent: Sep. 20, 2011

(54) HERMETICALLY SEALED THREE-DIMENSIONAL ELECTRODE ARRAY

(75) Inventors: Joseph H. Schulman, Santa Clarita, CA (US); Guangqiang Jiang, Santa Clarita, CA (US); Charles L. Byers, Canyon Country, CA (US)

(73) Assignee: Alfred E. Mann Foundation for Scientific Research, Santa Clarita, CA (US)

( * ) Notice: Subject to any disclaimer, the term of this patent is extended or adjusted under 35 U.S.C. 154(b) by 1022 days.

(21) Appl. No.: 11/380,877

(22) Filed: Apr. 28, 2006

(65) Prior Publication Data

US 2007/0067007 A1  Mar. 22, 2007

Related U.S. Application Data

(60) Provisional application No. 60/685,032, filed on May 25, 2005.

(51) Int. Cl.
*A61N 1/05* (2006.01)

(52) U.S. Cl. ........ 600/372; 600/373; 600/377; 600/378; 607/2; 607/115; 607/116

(58) Field of Classification Search .................. 600/372, 600/378, 384, 386, 393, 395, 464; 607/45, 607/46, 115, 116, 118
See application file for complete search history.

(56) References Cited

U.S. PATENT DOCUMENTS

| | | | |
|---|---|---|---|
| 4,837,049 A | 6/1989 | Byers et al. | |
| 4,852,573 A | 8/1989 | Kennedy | |
| 4,969,468 A | 11/1990 | Byers et al. | |
| 4,979,511 A * | 12/1990 | Terry, Jr. | 600/377 |
| 5,041,900 A * | 8/1991 | Chen et al. | 257/698 |
| 5,215,088 A | 6/1993 | Normann et al. | |
| 5,403,680 A | 4/1995 | Otagawa et al. | |
| 5,515,848 A * | 5/1996 | Corbett et al. | 600/377 |
| 6,008,980 A * | 12/1999 | Stevenson et al. | 361/302 |
| 6,026,326 A * | 2/2000 | Bardy | 607/40 |
| 6,171,239 B1 * | 1/2001 | Humphrey | 600/372 |

(Continued)

FOREIGN PATENT DOCUMENTS

WO  2004/093704 A  11/2004

OTHER PUBLICATIONS

Wise, K.D. and Angell, J.B., A Low-Capacitance Multielectrode Probe for use in Extracellular Neurophysiology, IEEE Transactions on Biomedical Engineering, May 1975, vol. BME-22, No. 3, pp. 212-219.

Klomp, G. F., Womack, M. V. B. and Dobelle, W.H., Fabrication of Large Arrays of Cortical Electrodes for Use in Man, Journal of Biomedical Materials Research, John Wiley & Sons, 1977, vol. 11, pp. 347-364.

(Continued)

*Primary Examiner* — Carl H Layno
*Assistant Examiner* — Allen Porter, Jr.
(74) *Attorney, Agent, or Firm* — Gary D. Schnittgrund

(57) ABSTRACT

The electrode array is a device for making electrical contacts with cellular tissue or organs. The electrode array includes an assembly of electrically conductive electrodes arising from a substrate where the electrodes are hermetically bonded to the substrate. The electrodes also include an insulating layer which leaves at least one zone or at least one hole exposed for making focused electrical contact with the tissue. A hole passing completely or partially through the electrode may further provide an anchor to the living tissue, thereby stabilizing the array with respect to the tissue being examined. Also, a method of manufacture of an electrode array and associated circuitry is disclosed.

24 Claims, 6 Drawing Sheets

U.S. PATENT DOCUMENTS

| | | |
|---|---|---|
| 6,277,116 B1 * | 8/2001 | Utely et al. ............... 606/42 |
| 6,458,157 B1 | 10/2002 | Suaning |
| 6,690,959 B2 * | 2/2004 | Thompson ............... 600/372 |
| 7,212,851 B2 * | 5/2007 | Donoghue et al. ........... 600/544 |
| 7,456,012 B2 * | 11/2008 | Ryttsen et al. ............. 435/285.2 |
| 2002/0038134 A1 * | 3/2002 | Greenberg et al. ............. 607/1 |
| 2003/0100823 A1 | 5/2003 | Kipke et al. |
| 2004/0006264 A1 * | 1/2004 | Mojarradi et al. ........... 600/378 |
| 2004/0176828 A1 * | 9/2004 | O'Brien ............... 607/119 |
| 2005/0004567 A1 | 1/2005 | Daniel et al. |
| 2006/0009814 A1 * | 1/2006 | Schulman ............... 607/45 |
| 2006/0085056 A1 * | 4/2006 | Schouenborg ............. 607/148 |
| 2007/0197892 A1 * | 8/2007 | Shen et al. ............... 600/378 |

OTHER PUBLICATIONS

Ko, W. H., Solid-State Physical Transducers for Biomedical Research, IEEE Transactions on Biomedical Engineering, Feb. 1986, vol. BME-33, No. 2, pp. 153-160.

Fofonoff, T.A., Martel, S.M., Hatsopoulos, N. G., Donoghue, J.P. and Hunter, I.W.., Microelectrode Array Fabrication by Electrical Discharge Machining and Chemical Etching, IEEE Transactions on Biomedical Engineering, vol. 51, No. 6, Jun. 1, 2004, pp. 890-895.

* cited by examiner

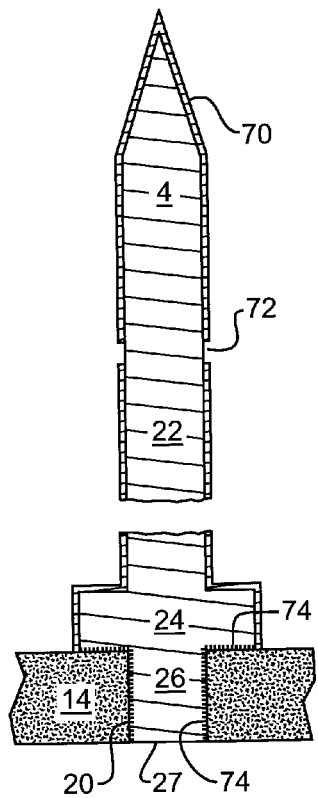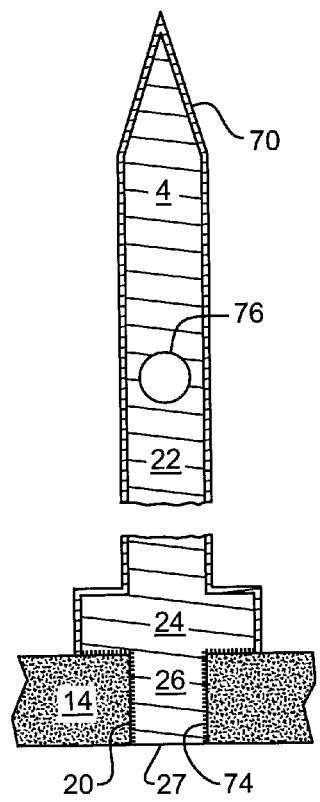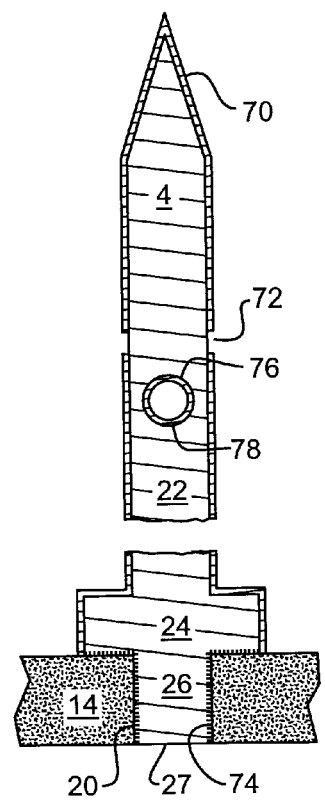
Fig. 7
Fig. 8
Fig. 9

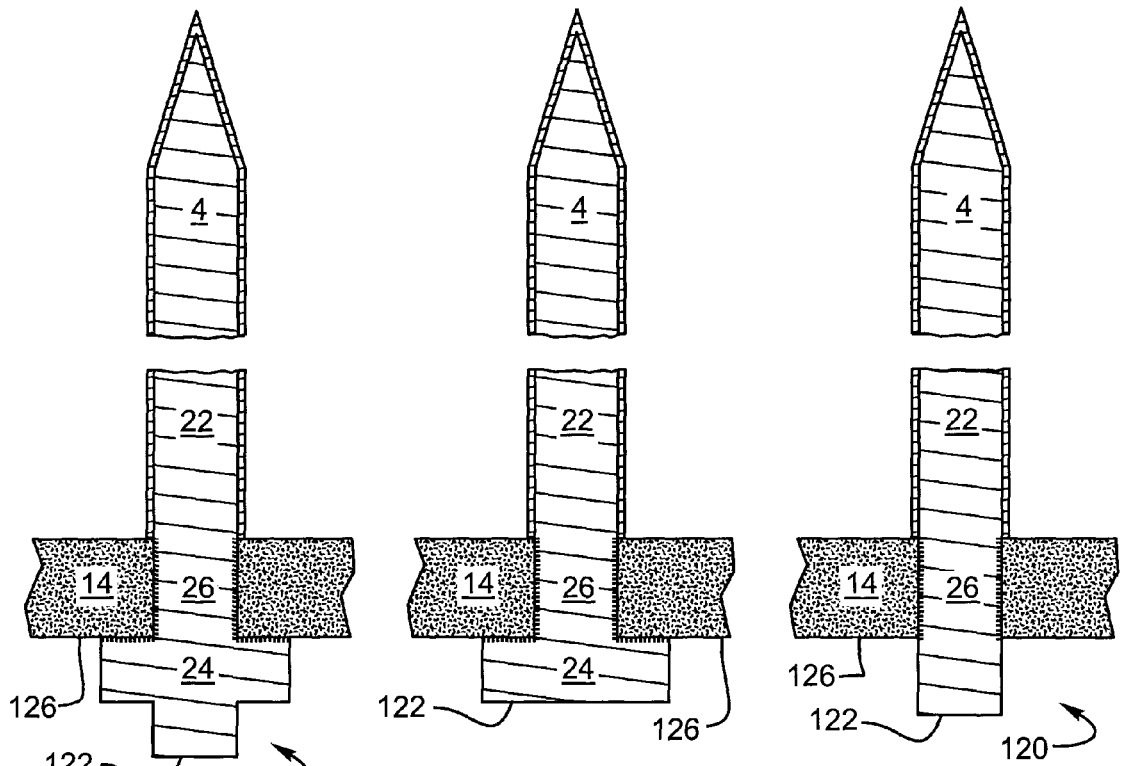
Fig. 13  Fig. 14  Fig. 15
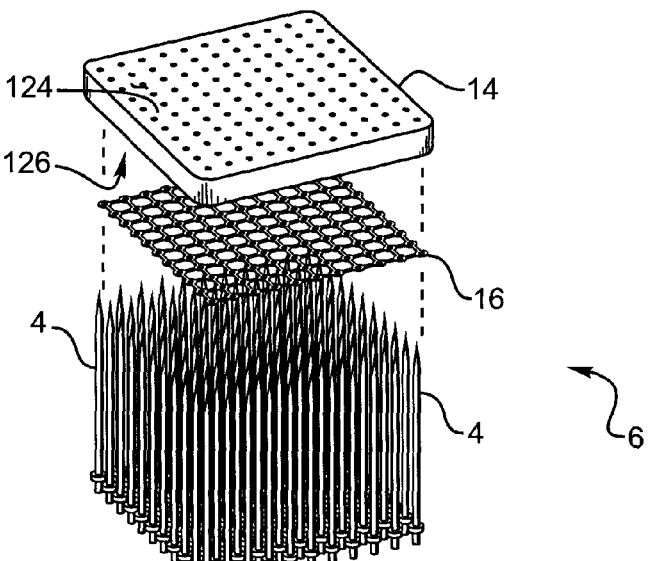
Fig. 16

HERMETICALLY SEALED THREE-DIMENSIONAL ELECTRODE ARRAY

CROSS REFERENCE TO RELATED APPLICATION

This application claims the benefit of U.S. Provisional Application Ser. No. 60/685,032, filed on May 25, 2005.

BACKGROUND OF THE INVENTION

1. Field of the Invention

This invention relates to a hermetically sealed three-dimensional electrode device and a method of manufacturing such a device. The device may be particularly useful for neuron interface and more specifically as a cortical implant.

2. Description of Related Art Including Information Disclosed Under 37 CFR 1.97 and 1.98

A nerve is a cordlike structure which is composed of numerous nerve fibers conveying impulses between a part of the central nervous system and some other region of the body. A nerve is made up of individual nerve fibers with their sheaths and supporting cells, small blood vessels, and a surrounding connective tissue sheath. Each nerve fiber is surrounded by a cellular sheath (neurilemma) from which it may or may not be separated by a laminated lipo-protein layer (myelin sheath). A group of such nerve fibers surrounded by a sheet of connective tissue (perineurium) is called a fasciculus. The fasciculi are then bound together by a thick layer of connective tissue (epineurium) to form the nerve.

Neurologists have long sought an electrode device which could establish stable electrical contact with a large number of individual nerve fibers within a nerve or a large number of individual neurons. Such a device would find wide medical application for sensing neurological impulses, facilitating the analysis and interpretation of such impulses, and delivering electrical stimuli to target nerve fibers as a reaction to such analysis or as a result of external input. The ideal electrode device would be adapted to the anatomy of the nerve so that it could penetrate the nerve in a nondestructive fashion in order to form focused electrical contacts with a very large number of individual nerve fibers.

Nerve cuff electrodes are employed in the neurological sciences for sensing nervous impulses and for electrically stimulating nerves. The nerve cuff electrode encircles the entire nerve and senses gross nervous impulses arising from the nerve fibers within the nerve. The nerve cuff electrode may also be employed to electrically stimulate the nerve. Individual nerve fibers within a nerve may be functionally distinct from the other nerve fibers. The utility of the nerve cuff electrode is limited by its inability to specifically direct signals to or from selected nerve fibers within the nerve.

In order to make electrical contact with individual nerve fibers within a nerve, narrow gauge needle electrodes may be employed. When a narrow gauge needle is inserted into the nerve, there is a chance that it may make electrical contact with an individual nerve fiber or a small number of such fibers. If electrical contact is desired with each of several nerve fibers, then several needle electrodes must be employed. However, the technique of using multiple needle electrodes becomes progressively more and more difficult as the number of electrodes increases. Hence, there is a limit to the number of needle electrodes which can be usefully employed on a single nerve. Also, the electrical contact between a needle electrode and its corresponding nerve fiber can be disrupted by muscle motion and other forms of motion, since the end of the needle opposite the electrode extends outside the nerve and can be levered by relative motion of neighboring tissues. Therefore, long term implantation of needle electrodes with stable electrical contact with nerve fibers is not possible with prior art needle electrodes.

An electrode array having several electrodes integrated into one device is disclosed by Robert L. White. (Proc. First International Conference on Electrical Stimulation of the Acoustic Nerve as a Treatment for Profound Sensorineural Deafness in Man, pub. by Velo-Bind, Inc. (1974), ed. by Michael M. Merzenich, et al., entitled "Integrated Circuits and Multiple Electrode Arrays," pp 199-207, by Robert L. White). White's electrode array employs a prong shaped base fabricated from a silicon wafer. The silicon base supports an array of electrodes which are deposited thereon toward the end of the prong. Each of the electrodes is small, flat, and circular, about 50 micrometers in diameter. Each electrode is connected to a corresponding conductor which carries signals to and from the electrode. The conductor is electrically insulated from the tissue by a layer of silicon dioxide. In use, the prong is inserted tip first into neural tissue. Neural tissue is displaced by the prong as it is inserted. Substantial damage to neural tissue can result from the insertion process due to the relatively large bulk of the prong. Since neural tissue slides tangentially past the electrodes during the insertion process, the flatness of the electrodes helps to minimize the resultant disruption and destruction of neural tissue. Once the device is inserted, the flatness of the electrodes limits the contact between the electrode and the neural tissue. Flat electrodes can make electrical contact only with neural tissue which is directly adjacent to the surface of the prong.

Multiple electrode devices with microelectrode tips protruding beyond and in a plane parallel to a silicon carrier (i.e. planar electrodes) are disclosed by Wise, et al. (IEEE Transactions on Biomedical Engineering, vol. BME-17(3), pp 238-247, July 1970, "An Integrated Circuit Approach to Extracellular Microelectrodes," and vol. BME-22(3), May 1975, "A Low-Capacitance Multielectrode Probe for Use in Extracellular Neurophysiology") and by Ko (IEEE Transactions on Biomedical Engineering, vol. BME-33, pp 153-162, February 1986, "Solid State Physical Transducers for Biomedical Research"). Wise teaches that the lateral spacing and length of the protruding tips may be controlled to produce various planar electrode arrays. Like the White device, the silicon carrier of the Wise and Ko devices have the shape of a prong and may cause significant tissue damage to the nerve during the insertion process. Also, if the Wise and Ko prong-shaped devices are implanted, their large bulk compromises the stability of the electrical contact between the electrode tips and individual target cells. Additionally, the thinness of the prong can make it susceptible to shear damage with side loading. Further, since the silicon carrier and the electrode tips are essentially coplanar with the tips cantilevered freely beyond the end of the carrier, the carrier imparts little if any transverse stability to the fragile tips during insertion of the Wise, et al. and Ko prong-shaped devices or after their implantation. Moreover, the number of useful electrodes which may be incorporated into the Wise and Ko devices is inherently limited. Since the electrode tips are aligned in a row along the edge of the silicon carrier, it is not possible to array the electrodes into a configuration with more than one dimension.

Known "bed of nails" devices are disclosed by Byers, et al. in U.S. Pat. Nos. 4,837,049 and 4,969,468 and by Normann, et al. in U.S. Pat. No. 5,215,088, all of which are incorporated herein by reference. These inventions relate to electrodes for electrically sensing or stimulating living tissues. In particular, the invention relates to electrode arrays and to methods for making and using such arrays. The tips of the needles may be left exposed by a dielectric coating. Below the needle is a metallic layer upon which the conductors are formed. The dielectric may be silicon dioxide. However, these devices are difficult to seal "hermetically", as is required when they are part of a "smart" array containing electronic signal processing means.

The needles may be constructed as "cones" and a method of construction may use techniques similar to those taught in U.S. Pat. Nos. 3,755,704, 3,789,471, and 3,812,559, each naming Charles A. Spindt, et al. as inventors U.S. Pat. No. 3,453,478, naming Kenneth R Soulders and Louis N. Heynick as inventors, also discloses background technology for constructing cones. Further disclosure on known fabrication technology may be found in an article by C. A. Spindt, et al., entitled "Physical Properties of Thin-Film Field Emission Cathodes with Molybdenum Cones," J. App. Phys., vol. 47 (12) December 1976.

Evaporating metal to form the needles of platinum, activated iridium, platinum-iridium alloy, rhenium, or other suitable implantable electrode material is presented.

Thus, what is missing and what is needed by practicing neurologists is an implantable electrode device which can electrically contact a large number of individual cells within an organ or tissue for sensing and/or controlling various bodily functions. The individual contacts should each be focused within a small region so that they involve single cells. However, the range of the contacts should extend over a relatively large region within the organ or tissue. The electrodes of the device should make positive contact with target cells, be firmly anchored, and should be stable over long periods of time, even with recurrent movement in adjacent tissues. On the other hand, the device should penetrate the target organ without being intrusive so that tissue damage to the target organ is minimal. The device should have a small volume and a robust construction for practical medical applications.

BRIEF SUMMARY OF THE INVENTION

The electrode array of the present invention is a device for establishing stable electrical contact with living tissue. In the preferred embodiment, the electrode array has a configuration for making multiple extracellular contacts and for conducting electrical signals to or from each cell with which there is contact. However, the electrode array can also be employed for measuring the voltage potential of the surface of organs and tissues, e.g. for EKG or EEG.

The electrode array includes a base of semiconducting or nonconducting material having a support surface, an array of conducting electrodes which extend substantially perpendicular to and from the support surface of the base and serve as electrodes and conductors incorporated onto or in the base and connected to the electrodes for carrying electrical signals to and/or from such electrodes. The invention also includes various embodiments of the electrode array and methods for using and fabricating such electrode arrays.

In a preferred embodiment of the electrode array, the electrodes are coated with an insulating layer of dielectric material, except for an uncoated area, such as a revealed band or a hole through the needle. This feature narrows and focuses the contact area of each electrode to a relatively small region and facilitates the ability of the electrode to contact single cells or small groups of cells.

Other objects and features will be apparent from the following description together with the drawings.

BRIEF DESCRIPTION OF THE SEVERAL VIEWS OF THE DRAWINGS

FIG. 7 presents a cross-sectional view of a coated electrode with a revealed conductive band.

FIG. 8 presents a cross sectional view of a coated electrode with a conductive through-hole.

FIG. 9 presents a cross-sectional view of a coated electrode with a coated through-hole and a revealed conductive band.

FIG. 13 is a cross-sectional view of a coated electrode that has been inserted through the bottom surface of the substrate.

FIG. 14 is a cross-sectional view of a coated electrode that has been inserted through the bottom surface of the substrate.

FIG. 15 is a cross-sectional view of a coated electrode that is inserted through the bottom surface of the substrate.

FIG. 16 is an exploded view of the electrode array, braze preform, and substrate, where the electrode is inserted from the bottom surface of the substrate.

DETAILED DESCRIPTION OF THE INVENTION

Figure 1:
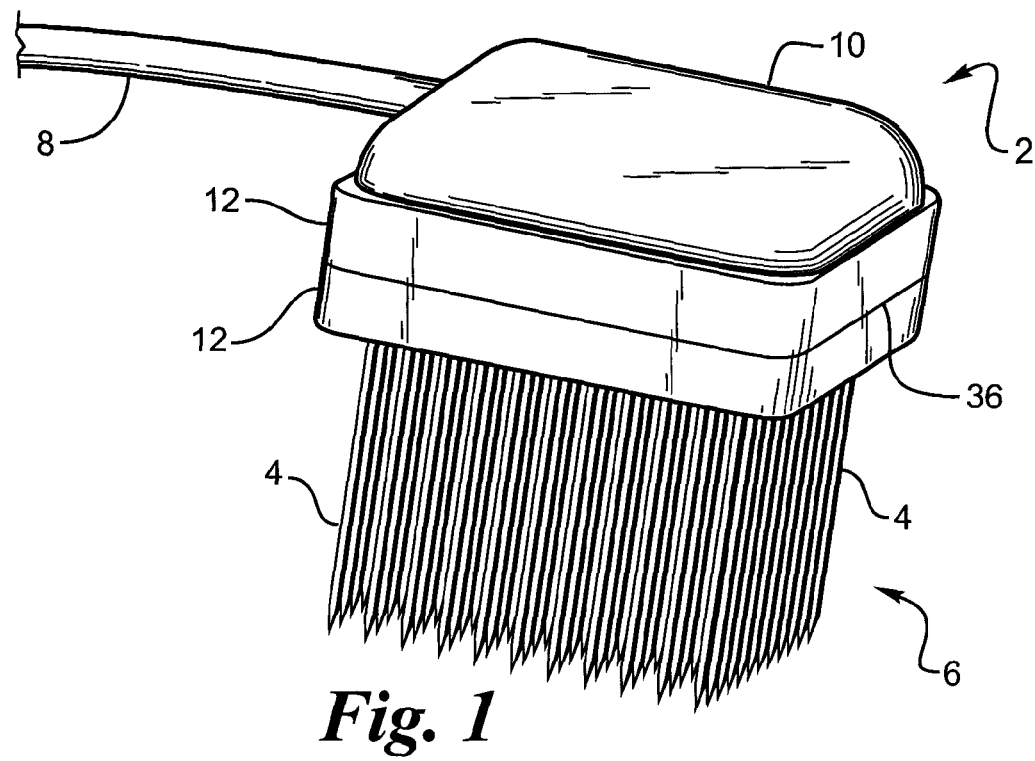
FIG. 1 is a perspective view of one embodiment of the electrode array illustrating an array of sharp electrodes arising from the substrate, a cable, and header. The array of sharp needles illustrates the concept of "bed-of-nails."

The invention, FIG. 1, is an electrode array 6, also known as a "bed-of-nails", which is applied to living tissue to provide an effective electrical connection therewith, whether for sensing or stimulating purposes. The electrode array 6 provides a multiple possibility of successful electrical contact, and causes minimal damage or upset to either the living tissue or to the body system. The electrode array 6 includes an arrangement of electrically conductive needles that arise from a substrate 14, are substantially normal thereto, and which serve as electrodes 4 (FIG. 2) for sensing or stimulation of living tissue. Terminals and electrical conductors may be employed to connect individual electrodes 4 or groups of electrodes of the electrode array 6 to other electrical circuits.

The bed-of-nails package 2 consists of the electrodes 4, which form an array 6 that may be in a planar, square or rectangular arrangement having regular spacing intervals, as depicted in the various embodiments presented in FIGS. 1 to 9 and 13 to 16, or which may be in an irregular or non-repetitive arrangement such as may be dictated by the desired function of the package 2. While the package 2 is presented as a generally rectangular package having rounded edges and corners, it may advantageously have a flat circular or ovaloid shape or other shape without limitation to those shapes just disclosed. The package 2 may have a thickness of about 2 mm, plus the length of the electrodes. In a preferred embodiment, the electrode 4 is about 0.5 to 4.0 mm (0.02 to 0.16 inches) in length and about 0.02 to 0.10 mm (0.001 to 0.004 inches) in diameter. Aspect ratios (height to diameter) of 40:1 are readily achievable. In the embodiment presented, the electrode array 6 contains about 121 electrodes 4 in a square matrix. The electrodes 4 may, of course, be taller and narrower. Electrode spacing in the array may vary, as may the size of the needles. Of course, such electrodes 4 may be conical or other elongated shapes. The spacing of the electrodes 4, transversely across a nerve, would be from approximately 0.5 micrometer to on the order of 100 micrometers. "On the order of" means within the range of 0.1 to 10 times the dimension, in this context and as used herein. Spacing of the electrodes 4 along the length of a nerve might well be greater than the lateral spacing of the electrodes 4 across the nerve. That is, the spacing distance between electrodes 4 along the length of a nerve can vary a great deal. Electrodes 4 or electrode array 6 might well be longitudinally spaced 1,000 micrometers, 2,000 micrometers, etc., from one another, depending on the desired density of electrical contact with the nerve. The package 2 may be planar or may be alternately shaped to conform to a specific desired application, although only planar arrays are presented in FIGS. 1 to 9 and 13 to 16. The electrode 4 material is biocompatible and is not limited to but may be selected from titanium, titanium alloy, platinum, platinum alloy, activated iridium, platinum-iridium alloy, conductive polymer, carbon or other suitable electrically conductive material known by those skilled in the art as suitable for use in connection with the body. In general, metals or other conductive substances which are inert and are least subject to corrosion are selected. In the case of stimulating devices, conductive materials which can handle the necessary current densities are required. In a preferred embodiment, the electrodes 4 are comprised of an electrically conductive and biocompatible material which may be elemental metals or alloys, such as but not limited to a titanium alloy, such as Ti-6Al-4V, Ti-5Al-2.5Fe, Ti-6Al-2Sn-4Zr-2Mo, Ti-6Al-6V-2Sn, or Ti-4Al-4Mo-2Sn—Si, or a platinum alloy, such as 90Pt-10Ir or 80Pt-20Ir, or pure platinum, or pure iridium. As will be discussed herein, coatings may be employed to enhance the stability of the electrodes 4. Candidate coating materials include, but are not limited to, gold, platinum, iridium, platinum oxide or iridium oxide, or another coating that is suitable for electrode application. The coating is applied to the electrode 4 surface at least where the electrode 4 is exposed to living tissue, as it is at a reveal 72 or at an uncoated through-hole 76.

The electrodes 4 must, therefore, be spaced according to the specific application. The electrodes 4 should be small and of the correct sharpness to avoid damaging the nerve. Also the electrically conductive portion of each electrode 4 should be small enough to contact only a single fiber and thereby obtain signals from only one fiber. Consequently, a preferred embodiment of the invention is to insulate the electrode, except at selected location or locations between a distal end 80 and a proximal end 82 of the electrode 4, so that at least one electrically conductive portion of each electrode 4 is exposed. In this way, each electrode 4 may be designed to contact the living tissue at one location or at multiple locations, if more than one electrically conductive portion of the electrode 4 is exposed to effect electrical contact more than one fiber of living tissue.

In addition, the electrodes 4 must be high or long enough to assure sufficient penetration of the desired nerve so as to make electrical connection with the nerve fiber inside the nerve. In order to reach the nerve fiber, the sheath and other connective tissues must be penetrated. However, "electrical connection" or "contact" with a nerve fiber or other body tissue may mean actual physical contact with the nerve fiber or tissue or it may mean being in sufficiently close location to sense the electrical signals therefrom or to stimulate the fiber or tissue.

The electrode 4 spacing and length may vary on a given substrate 14. In order to reach down into a fissure in the brain, for example, it may be desirable to have longer electrodes 4 on one portion of the electrode array 6 and shorter electrodes 4 on another portion. Also, spacing density on one portion of the electrode array 6 may be greater or lesser than on another portion. The term "electrode array" as used herein means a collection of electrodes and includes systematic and orderly groupings or arrangements as well as including non-linear and irregular groupings or arrangements, which may be dictated by the function to be served by the electrode array. There may be an abrupt change of electrode 4 length or density, or both, in one or more directions. There may be graded or gradual changes in one or more directions.

It is to be understood that the array 6 may be sized to fit the particular application and may be planar, multiplanar, curved, twisted, or other desired shape as required in the particular circumstances involved. Ordinarily, the electrode array 6 is disposed on a rigid substrate 14. However, it is to be appreciated that the substrate 14 may be flexible, or that the electrode array 6 may be comprised of electrodes 4 on a plurality of substrates 14. In general, the electrodes 4 in an array 6 should be held in relatively fixed spacing with respect to each other. It is intended to cover by "relatively fixed" terminology, instances in which the substrate 14 is flexible, curved, stretchable, etc.

Among the suitable substrates 14 are, without limitation, ceramics, such as zirconia, more specifically stabilized-zirconia, partially-stabilized zirconia, tetragonal zirconia polycrystal, magnesia-stabilized zirconia, ceria-stabilized zirconia, yttria-stabilized zirconia, and calcia-stabilized zirconia, as well as silicon, sapphire, alumina, or germanium. Biomedical grade plastics may also be used such as the polyamides, polyimides, polymethacrylates, acrylics, polycarbonates, etc., to the extent that such plastics may be implantable or rendered implantable. These plastics cannot form a braze bond and, more importantly, they do not form a hermetic device.

The electrodes 4 may be arranged in random fashion or ordered in columns and/or rows or other ordered arrangements. The optimum embodiment from the standpoint of orderly electrical connection is an ordered arrangement. One embodiment which may be desired is that in which each electrode 4 (except, of course, those near the edges of the array 6) is surrounded by six other electrodes 4, all equidistantly spaced. The electrodes 4 are electrically connected to a terminal which may, likewise, be randomly located or located in orderly columns and/or rows. The terminal may include bonding pads which provide an electrical connection between the electrodes 4 and other electrical circuits. Connection points need not be in the same arrangement as the electrodes 4. Thus, the electrodes 4 may be located in columns, but not rows, and the terminals may be located in columns and rows.

In addition, the package 2 is comprised of a case 12 that may have two halves, as illustrated in FIG. 1. The two halves of case 12 are welded together at weld 36 to form a hermetic seal. The case is comprised of biocompatible materials, which in a preferred embodiment may be titanium or an alloy of titanium that is weldable.

Cable 8 transmits electrical signals to and/or from the package 2 and is electrically connected to the electrodes 4 in a manner to assure that the desired function of the device is achieved. Header 10 electrically isolates the connections between the cable 8 and the electrodes 4. The isolation formed by the header 10 is not necessarily hermetic and may therefore be accomplished by forming header 10 of an epoxy material or a biocompatible electrically insulating material, which need not form a hermetic seal in the instant application, but which provide electrical isolation between the feedthrough pins 34. In a preferred application, the number of electrical conductors in cable 8 approximate the number of feedthrough pins 34.

A cross-section of the device 2 is presented (FIG. 2) showing the electrodes 4 in a flat, rectangular electrode array 6, where each electrode 4 is hermetically bonded to substrate 14. Electronic components 18 are presented and consist of integrated circuit chips, capacitors, and other electronic components that are known to those skilled in the art. Inclusion of signal processing as part of the device enables a "smart" array, wherein it is necessary to have hermetic and biocompatible packaging for the bed of nails and electronics. The case 12 covers and encloses electronic components 18 and forms a hermetic seal with substrate 14 by, for example, a braze joint 86. Feedthrough pins 34 are shown in a preferred embodiment as flat headed pins that are comprised of a conductive brazeable metal, such as titanium or its alloys, niobium or its alloys, platinum or its alloys, iridium or its alloys, or silver or its alloys. The feedthrough pins 34 are bonded by known processes, such as brazing or welding, to the electrical conductors in cable 8.

Figure 2:
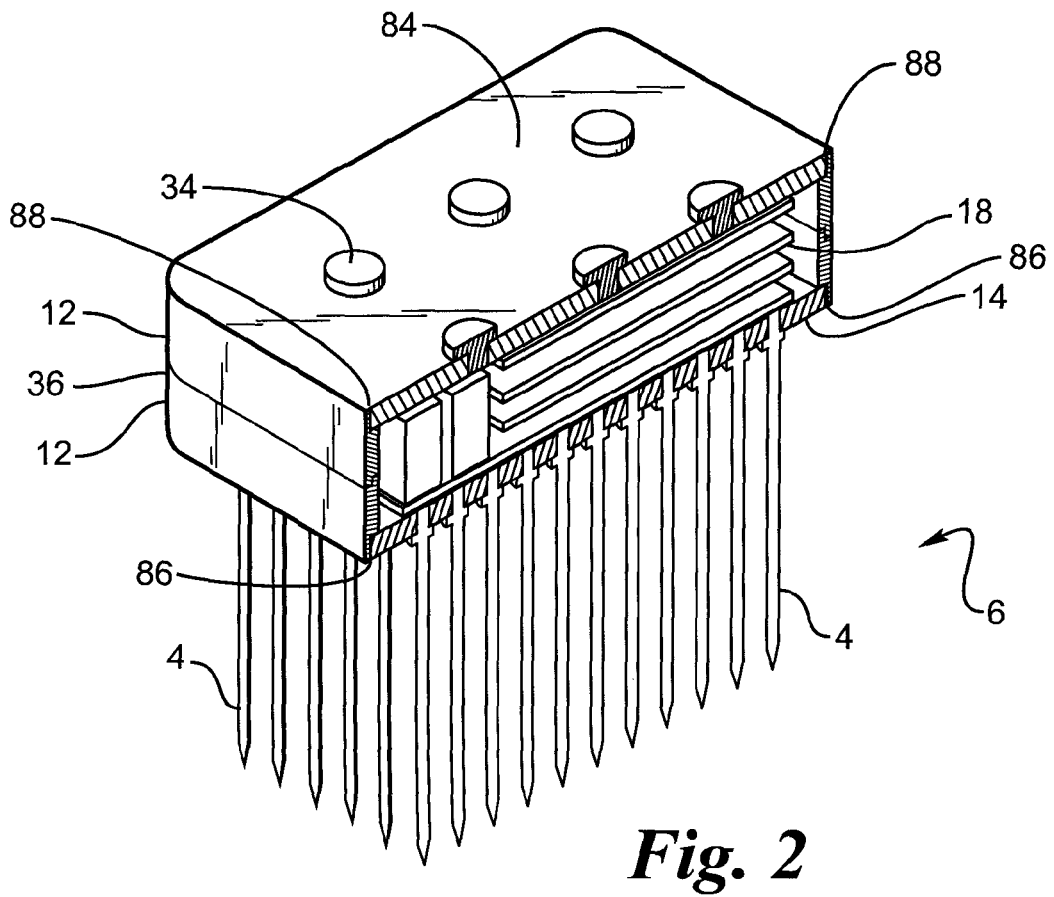
FIG. 2 is a cut-away of the perspective view of FIG. 1 illustrating the sharp electrodes passing through the substrate.

The embodiment of device 2 presented in FIG. 2 presents a preferred embodiment where a lid 84 is comprised of a material such as those candidates presented for substrate 14, notably zirconia or alumina. The lid 84 is attached by braze joint 88 to case 12, thereby forming a hermetic seal that protects electronics components 18. In alternate embodiments lid 84 may be comprised of a metal and may be comprised of the same material as case 12, potentially being an integral part of the assembly and thus avoiding joint 88.

Figure 3:
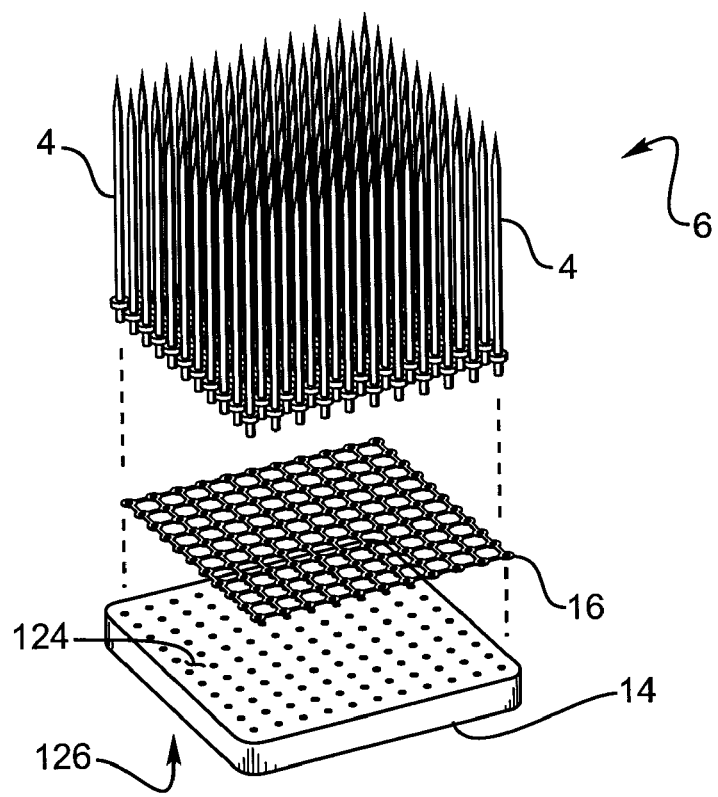
FIG. 3 presents an exploded view of the electrode array, braze preform, and substrate.

A sub-assembly to aid in describing the assembly process is presented in FIG. 3. In this embodiment the electrodes 4, while forming an electrode array 6, are inserted into a conforming braze preform 16, which is comprised of a braze material, from the top surface 124 of substrate 14. Substrate 14 receives a portion of each electrode 4 prior to being thermally processed to develop a hermetic seal between each electrode 4 and the substrate 14.

Figure 4:
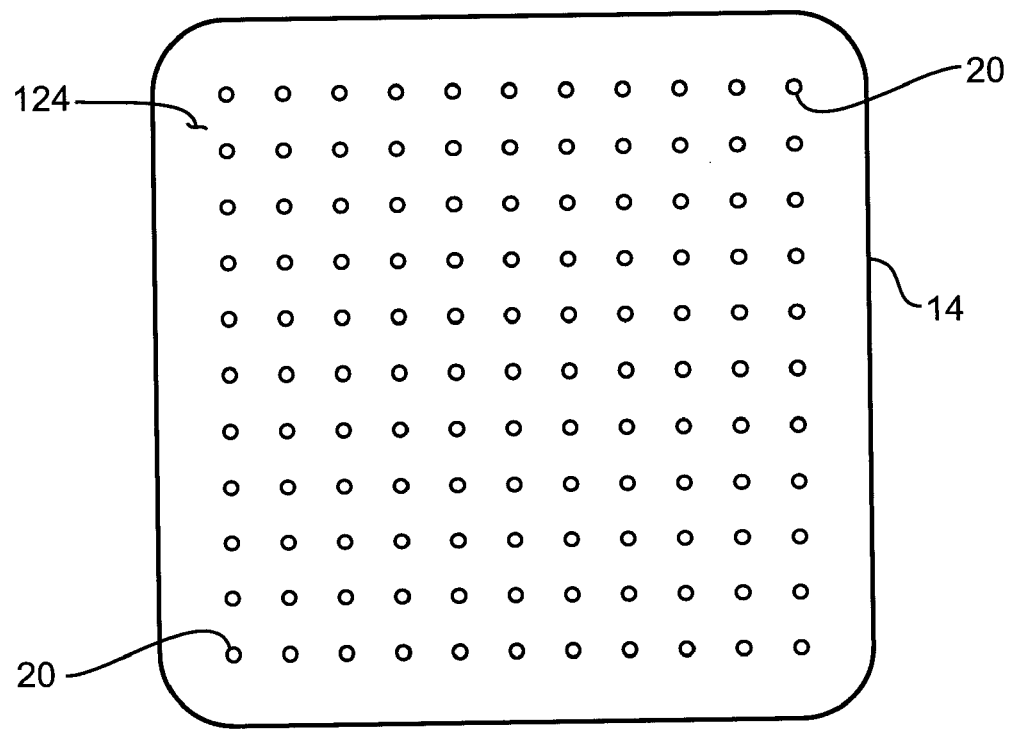
FIG. 4 is a top view of the substrate.
Figure 5:
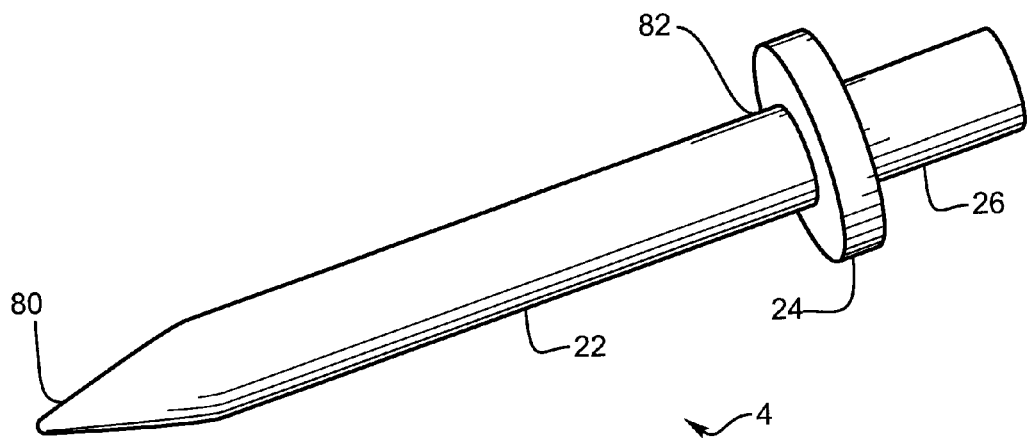
FIG. 5 is a perspective view of an electrode.

The substrate 14, FIG. 4, contains a number of feedthrough holes 20 which correspond to the number and configuration of electrodes 4 when they are arranged in the electrode array 6. The electrode 4, as presented in FIG. 5, consists of a shaft 22 which has a sharp end at its distal end 80, for tissue penetration during use, and an end that contacts brazing head 24 at its proximal end 82. The electrode then terminates with feedthrough 26 which, in the embodiment presented in FIG. 5, enters feedthrough hole 20 from the top surface 124 until brazing head 24 contacts braze preform 16, which in turn contacts substrate 14. A feedthrough 26 is comprised of a hole 20, braze joint 74, and electrode. Substrate 14 is preferably comprised of a ceramic, preferably zirconia.

Figure 6:
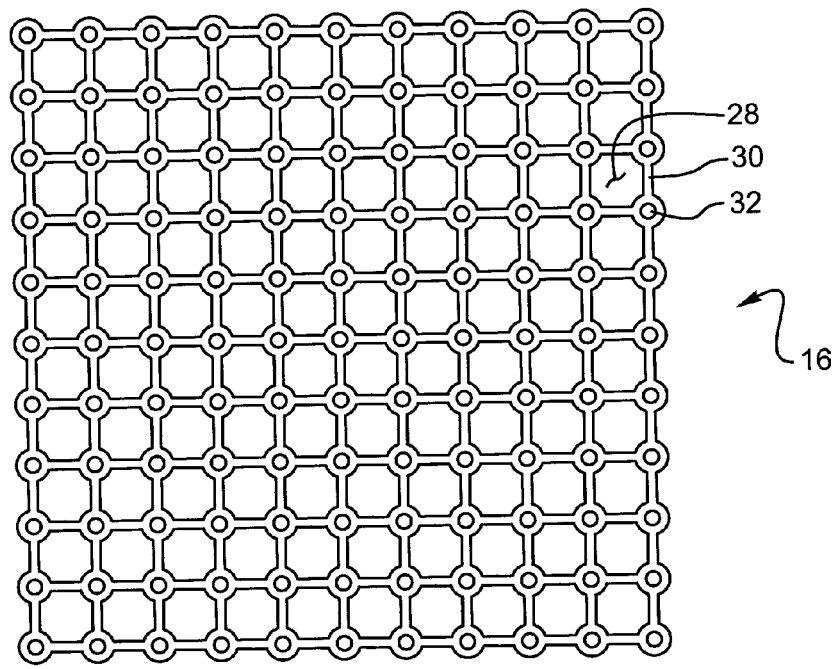
FIG. 6 is a top view of the braze preform.

Braze preform 16 is presented in FIG. 6 and is configured to have a hole 32 that corresponds to each substrate feedthrough hole 20, which in turn corresponds in approximate diameter and location to the electrode 4 and electrode array 6. The braze material of braze preform 16 forms a plurality of tabs 30 thereby forming a matrix of braze material as a layer or multiple layers of braze material which, when thermally processed, hermetically bonds the electrodes 4 to the substrate 14. A large non-functional opening or void 28 is formed by the interconnecting tabs 30 and holes 32. The tabs 30 may be removed after brazing by sandblasting, dicing, laser ablation, etc. so that individual electrodes are isolated from each other. Alternate embodiments of the braze preform 16 are conceived where the tabs 30 are removed and only a "braze washer" of material remains. Yet another embodiment of the braze preform 16 is a sheet of braze material that contains holes that accept the electrodes 4 in alignment with substrate feedthrough holes 20. The metal braze material may be, without limitation, an alloy, a composite, or a layered laminate that forms the desired thermally processed structure and is preferably comprised of nickel or an alloy of nickel, as disclosed in U.S. Pat. No. 6,521,350, which is incorporated by reference in its entirety. Also, U.S. patent application Ser. Nos. 10/697,149; 10/793,457, and 10/793,006, all of which are incorporated by reference in their entirety, disclose candidate braze materials.

The cross-sectional view of electrode 4 presented in FIG. 7 presents the shaft 22 in relation to the brazing head 24, which abuts substrate 14 and is attached thereto by braze material at a braze joint 74. The braze joint 74 continues along the interface formed between electrode feedthrough 26 and feedthrough hole 20. The proximal end of the electrode 4 comprises a contact surface 27 for connection to other electrical circuits. The electrode 4 is covered by electrically insulating coating 70 thereby preventing electrical contact with the tissue in which the electrode 4 is placed, except at the electrically conductive reveal 72, which in a preferred embodiment is presented as an uncoated band that circumscribes shaft 22. More than one reveal 72 may be placed on a given electrode 4 to enable monitoring several neural fibers, for example. Each fiber will have its own individual signal, which may be monitored individually by selecting the signal and utilizing electronic filtering to distinguish the several signals from each other. It is conceived that the distal tip 80 (FIG. 5) may be revealed also. The utilization of multiple reveals is most useful when electrical signals are being sensed, since in a stimulation mode, each reveal would stimulate each contact point simultaneously, while in the detection mode, the electronic package can discriminate between individual sensed inputs on a single electrode 4 having multiple reveals 72 or holes 76.

Coating 70 is comprised of a biocompatible and electrically insulating coating, such as parylene, polyimide, alumina, or zirconia. Coating 70 is preferably comprised of parylene, a well known organic coating that is biocompatible. Electrically conductive contact between tissue and electrode 4 is limited by the position, size, and shape of the reveal 72.

An alternative embodiment of the electrode 4 is presented in FIG. 8, wherein the electrode 4 is coated with insulating coating 70 except at through-hole 76, which in this embodiment passes completely through the shaft 22. The inside of hole 76 is left uncoated, where electrically conductive contact with the tissue occurs.

A further feature of the embodiment presented in FIG. 8 is that the living tissue, which may be a nerve bundle or an axon, grows into the hole 76 and thereby anchors the electrode in position in the tissue. Hole 76 need not pass completely through shaft 22 to provide an anchor for the ingrowth of tissue. The hole 76 has a diameter of about 0.01 to 0.03 mm (0.0005 to 0.001 inches) and may be fabricated by laser drilling.

Another alternative embodiment is presented in FIG. 9, where the hole 76 is electrically insulated and coated along its inside walls with coating 78, which is preferably the same coating as the coating 70 on the outside of electrode 4. In this embodiment the hole 76 provides an anchor to the living tissue. The reveal 72 provides electrical communication with the tissue.

Figure 10:
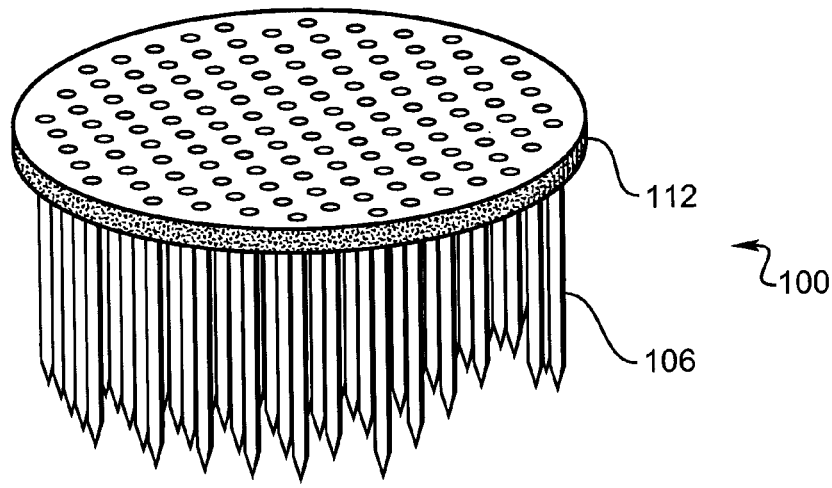
FIG. 10 is a perspective view of an embodiment of an electrode array illustrating an oval arrangement of irregular length electrodes.

A further embodiment of an electrode array 100 is presented in FIG. 10 wherein the electrodes 106, which are bonded to oval substrate 112, have variable lengths. The substrate 112 and electrode array 100 pattern may be oval, circular, rectangular, or an irregular shape without limitation. The reveals, not illustrated, may be located in one plane, at variable locations, or in a non-repeating pattern.

Figure 11:
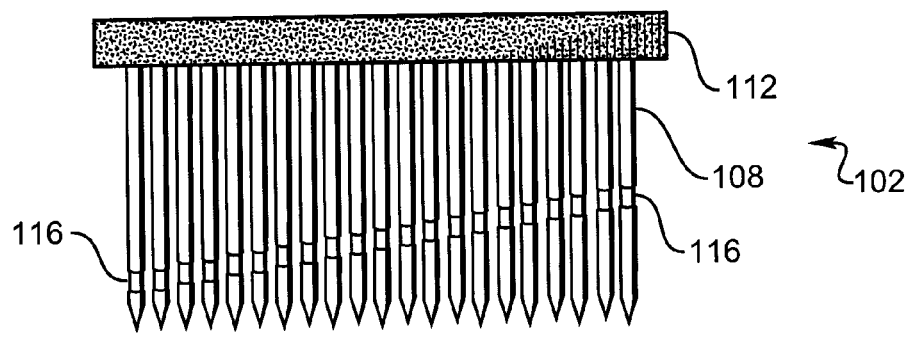
FIG. 11 is a side view of an embodiment of an electrode array illustrating equal length electrodes where the reveal is located at various locations along the electrode.

The embodiment presented in FIG. 11 presents electrode array 102 wherein the electrodes 108 are of equal length but each has a reveal 116 that is disposed at various locations along the length of electrode 108 such that contact with the living tissue occurs with different tissue bundles, for example. While not illustrated, it is envisioned by the inventors that the spacing between electrodes 108 may be variable and need not be equidistant from each other.

Figure 12:
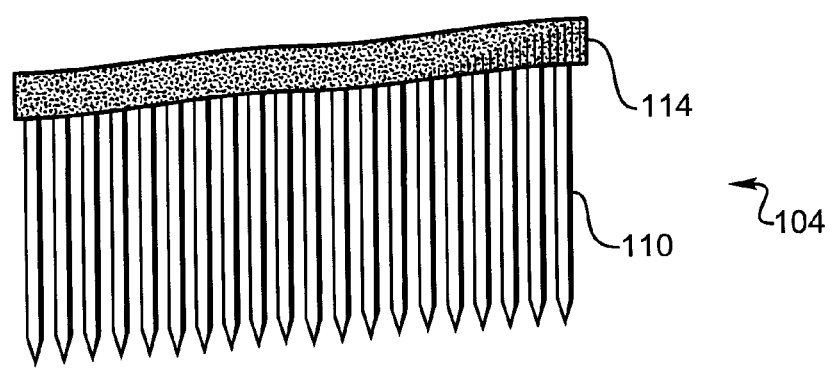
FIG. 12 is a side view of an embodiment of an electrode array on a non-flat irregular substrate where the electrode length varies.

The embodiment of FIG. 12 presents an electrode array 104 wherein the electrodes 110, which are bonded to non-flat, irregular substrate 114, have irregular lengths. The reveals, not illustrated, may be arranged in a multitude of arrangements, as described for FIG. 11.

The alternative embodiment of FIG. 13 presents the electrode 4 inserted through the substrate 14 from the bottom surface 126. The contact surface 122 of terminal 120 provides a connecting surface to the other electrical circuits. In this configuration, FIG. 13, the braze surface 74 is concealed from the living tissue environment.

FIG. 14 presents an embodiment that is similar to that of FIG. 13, except that presenting contact surface 120 is on brazing head 24, which results in a more readily formed electrode 4.

FIG. 15 is more readily formed than the electrode of FIG. 13 or 14 and contact surface 122 is formed on shaft 22.

The substrate 14, FIG. 16, contains a number of feedthrough holes 20 which correspond to the number and configuration of electrodes 4 when they are arranged in the electrode array 6. The electrode 4 then terminates with feedthrough 26 which, in the embodiment presented in FIG. 16, enters feedthrough hole 20 from the bottom surface 126 of substrate 14 until brazing head 24 contacts braze preform 16, which in turn contacts substrate 14.

Although the invention has been described and illustrated in detail, it is to be clearly understood that the same is by way of illustration and example only and is not to be taken by way of limitation, the spirit and scope of this invention being limited only by the terms of the appended claims.

What is claimed is:

1. An implantable electrode arrangement for establishing electrical contact with living tissue, the electrode arrangement comprising:
   a substrate having a plurality of feedthrough holes, a top surface and a bottom surface;
   a plurality of electrically conductive electrodes, each electrode having a proximal end and a distal end, each electrode configured, at its proximal end, to be positioned within a feedthrough hole;
   each of said electrodes extending from said top surface, said electrodes hermetically bonded to said substrate;
   a dielectric coating covering and electrically insulating at least a portion of said electrodes; and
   at least one reveal zone not at the distal end on said electrodes, wherein the at least one reveal zone is sized to contact only a single nerve fiber.

2. The implantable electrode arrangement according to claim 1, wherein said reveal zone comprises a through-hole in at least one of said plurality of electrodes.

3. The implantable electrode arrangement according to claim 1, wherein at least one of said plurality of electrodes has a shaft that defines a through-hole that is coated by said dielectric coating covering.

4. The implantable electrode arrangement according to claim 1, wherein said electrodes are hermetically bonded to said substrate by brazing.

5. The implantable electrode arrangement according to claim 1, wherein said electrodes have a diameter of about 0.02 to 0.10 mm.

6. The implantable electrode arrangement according to claim 1, wherein said electrodes extend from said top surface with a range of heights from approximately 0.5 to 4.0 mm.

7. The implantable electrode arrangement according to claim 1, wherein said electrodes are adjacently spaced with a range from approximately 0.5 micrometers to on the order of 100 micrometers.

8. The implantable electrode arrangement according to claim 1, wherein said electrodes are comprised of titanium alloy, a platinum-iridium alloy, or a niobium alloy.

9. The implantable electrode arrangement according to claim 1, wherein said substrate is comprised of zirconia or alumina.

10. The implantable electrode arrangement according to claim 1, wherein said dielectric coating is comprised of parylene.

11. The implantable electrode arrangement according to claim 1, wherein said electrode is in registration with a respective one of the feedthroughs.

12. The implantable electrode arrangement according to claim 1, wherein a cable is electrically connected to at least one of said electrodes, whereby said reveal zone is capable of establishing electrical contact with the tissue and the electrode arrangement is capable of establishing an arrangement of electrical contacts with the tissue.

13. The implantable electrode arrangement according to claim 12, wherein:
   said electrodes perpendicularly extend from said top surface with a range of heights from approximately 0.5 to 4.0 mm, and
   said electrodes are adjacently spaced with a range from approximately 0.5 micrometers to on the order of 100 micrometers.

14. The implantable electrode arrangement according to claim 12, wherein the electrode arrangement electrically contacts individual cellular components of the living tissue and wherein each reveal zone of said electrodes is sufficiently small to be capable of making electrical contact with a single cellular component within the tissue.

15. The implantable electrode arrangement according to claim 12, wherein said dielectric coat covering is comprised of a biocompatible composition for rendering the electrode arrangement implantable into the living body.

16. The implantable electrode arrangement according to claim 1, wherein said reveal zone is coated with platinum, iridium, or their oxides.

17. An implantable electrode arrangement for establishing electrical contact with living tissue, the electrode arrangement comprising:
   a substrate having a plurality of feedthroughs;
   a plurality of electrically conductive electrodes, each electrode having a proximal end and a distal end with a reveal zone sized to contact only a single nerve fiber therebetween, each electrode
configured, at it proximal end, for electrical communication with a respective one of the feedthroughs;

each of said electrodes extending substantially perpendicular from said substrate, each of said electrodes being hermetically bonded to said substrate; and a dielectric coating covering and electrically insulating said electrodes, exclusive of the reveal zone.

18. The implantable electrode arrangement of claim 17, wherein said electrodes are comprised of titanium alloy, a platinum-iridium alloy, or a niobium alloy.

19. An implantable electrode arrangement for establishing electrical contact with living tissue, the electrode arrangement comprising:

a plurality of electrically conductive electrodes defining an arrangement thereof, each electrode having a proximal end and a distal end;

said electrodes extending substantially perpendicular from a substrate, said electrodes being hermetically bonded to said substrate; and wherein each electrode has at least one reveal zone, sized to contact only a single nerve fiber, located between the proximal and distal ends, each electrode having a dielectric coat covering and electrically insulating at least a portion of said electrode.

20. The implantable electrode arrangement of claim 19, wherein said reveal zone further includes a reveal zone that is located at said distal end.

21. The implantable electrode arrangement of claim 19, wherein said reveal zones are located at various distances from said proximal end.

22. The implantable electrode arrangement of claim 19, wherein said distal ends are located at irregular distances from said proximal ends.

23. The implantable electrode arrangement of claim 19, wherein said reveal zone is comprised of at least one through-hole.

24. An implantable electrode arrangement for establishing electrical contact with living tissue, the electrode arrangement comprising:

a plurality of electrically conductive electrode, each electrode having a proximal end and a distal end, each electrode configured, at its proximal end, for electrical communication with a respective one of the feedthroughs;

each of said electrodes extending substantially perpendicular from a substrate, said electrodes being hermetically bonded to said substrate;

said electrodes having a plurality of reveal zones located between the proximal and distal ends, each electrode having a dielectric coating covering and electrically insulating at least a portion of said electrodes; and wherein each of the plurality of reveal zones is sized to contact only a single nerve fiber.

* * * * *